United States Patent [19]
Glad

[11] Patent Number: 6,156,550
[45] Date of Patent: Dec. 5, 2000

[54] METHOD OF NON-ADHESIVE COATING OF A SYNTHETIC POLYMER BASED SURFACE WITH PARTICLES

[75] Inventor: Gunnar Glad, Knivsta, Sweden

[73] Assignee: Pharmacia Biotech AB, Uppsala, Sweden

[21] Appl. No.: 09/012,985

[22] Filed: Jan. 26, 1998

Related U.S. Application Data

[63] Continuation of application No. 08/432,114, filed as application No. PCT/SE93/00928, Nov. 5, 1993.

[30] Foreign Application Priority Data

Nov. 6, 1992 [SE] Sweden .................................. 9203319

[51] Int. Cl.$^7$ ..................... C12N 11/08; G01N 33/545; G07K 17/08
[52] U.S. Cl. .................... 435/180; 427/307; 436/531; 530/413; 530/815
[58] Field of Search ................... 422/55–57, 90; 435/174, 177, 180; 436/523, 528–531, 534, 535, 826; 530/402, 412, 413, 417, 815; 427/307

[56] References Cited

U.S. PATENT DOCUMENTS

| 3,993,451 | 11/1976 | Verbeck . | |
| 4,465,751 | 8/1984 | Kawamura et al. | 430/64 |
| 4,801,665 | 1/1989 | Getman et al. . | |
| 5,098,569 | 3/1992 | Stedronsky | 210/500.29 |
| 5,246,737 | 9/1993 | Muradov | 427/307 |

FOREIGN PATENT DOCUMENTS

| 0420053 | 4/1991 | European Pat. Off. . |
| 0501735 | 9/1992 | European Pat. Off. . |
| 2000975 | 9/1969 | France . |
| 49-40873 | 11/1974 | Japan . |

OTHER PUBLICATIONS

Merkos et al., Nucleic Acids Research, vol. No. 7, 1679–1684 (1992).
Derwent Abstracts 74–83716v (1994).
WPIDS Abstract 71–35653T (1969).

*Primary Examiner*—David M. Naff

[57] ABSTRACT

A synthetic polymer based surface is coated with polymer particles without the use of an adhesive. A top surface layer is swollen or semidissolved by contacting with a solvent such as acetone, polymer particles are contacted with the surface to partially embed the particles in the surface layer, and the surface layer is dried. The polymer particles are either dry or in a slurry when contacted with the surface, and contact with the polymer particles may be simultaneous or subsequent to contacting with the solvent. The particles may be particles for chromatography, and may be derivatized before or after contacting with the surface such as by coupling an enzyme, DNA, an antibody or an antigen.

10 Claims, No Drawings

METHOD OF NON-ADHESIVE COATING OF A SYNTHETIC POLYMER BASED SURFACE WITH PARTICLES

This application is a continuation of application Ser. No. 08/432,114, filed on May 5, 1995, now abandoned. Application Ser. No. 08/432,114 is the national phase of PCT International Application No. PCT/SE93/00928 filed on Nov. 5, 1993 under 35 U.S.C. § 371. The entire contents of each of the above identified applications are hereby incorporated by reference.

BACKGROUND OF THE INVENTION

1. Field of the Invention

The present invention relates to surface modification, and more particularly to a method of non-adhesive coating of a polymer based surface with particles.

2. Description of the Related Art

It is generally known in the prior art to modify surfaces of articles of plastic and other materials by immobilizing particles thereto, such as for increasing the wear resistance, for texturing purposes, for coating paper, for preparing photographic materials, for preparing analytical test systems, etc. The coating procedures used are, however, often complicated and in most cases involve the use of a binder which may have an adverse effect on the particles depending on the intended purpose of the coated product.

For example, U.S. Pat. No. 3,993,451 discloses a test sheet comprising a plastic film support having adhered to one surface thereof a layer of reagent-containing particles and reagent-free hydrophilic particles. The test sheet is prepared by applying the particles in dry form to the support which has prior thereto been sprayed with an adhesive.

EP-A-420 053 discloses an analytical test system comprising a flat porous sheet material with a protein non-absorptive polyurethane polymeric coating supporting particles coated by a bioaffinity agent. The particles are entrapped in the surface structure of the support material by applying a small amount of a buffer suspension of the bioactive agent-coated particles to the treated support followed by drying. More permanent attachment of the particles to the support may be achieved by covalently binding the antibody or other agent coated on the particles to the polymer-coated support by means of a cross-linking agent.

Maskos U. and Southern E. M., Nucl. Acids Res. 7 (1992) 1679–1684, discloses the fusion of ballotini glass beads to plastic sticks by dipping the sticks in molten polypropylene and then bringing them into contact with a pile of derivatized glass beads. The fused beads were then used as supports for oligonucleotides in nucleic acid hybridization.

SUMMARY OF THE INVENTION

The present invention proposes a significantly improved method of modifying a polymer based surface with particles, which method, on one hand, is simpler to perform than the prior art methods and, on the other hand, produces a better surface in terms of, for example, a denser packing of the particles, a more well-defined monolayer of the particles or a higher capacity with respect to the desired property or properties of the surface to be provided by the particle coating.

In accordance with the method of the invention, the top layer of the polymer based surface is converted to a swollen or semidissolved state without the use of adhesive. The particles with which the surface is to be coated are then applied, either simultaneously with or after the swelling or dissolution of the top layer.

The surface obtained by this method will support the particles firmly fixed thereto by being partially embedded in the top layer of the surface material, the particles protruding from the surface with their major surface area exposed and uncovered by any binder.

The polymer based article referred to above could be of any desired shape, such as a film, plate, ball, rod, pipe, pin, peg, multipronged device, etc.

In one embodiment of the method, the article surface is coated with particles of the desired shape, size and property by contacting the article with a mixture or slurry of the particles and a solvent capable of swelling or dissolving the article material, and then drying the article having the particles adhered to its surface.

In another embodiment of the method, the article surface is first treated with a solvent capable of swelling or dissolving the article material and then contacted with dry particles whereupon the surface is dried.

In still another embodiment of the method, the article surface is contacted with a solvent capable of swelling or dissolving the article material prior to contacting the article surface with the particle mixture or slurry of the first mentioned embodiment.

DETAILED DESCRIPTION OF THE INVENTION

The first method embodiment may be performed by dipping the cleaned article for a suitable period of time in the particle slurry followed by drying, such as by ambient or heated air, heat radiation or in vacuo. The dip time depends on the article material and the solvent as well as on the desired dissolution depth of the surface layer. Usually the dip time is rather short, for example 1 to 10 seconds. The dissolution depth will, of course, also depend on the temperature. The method is, however, usually conveniently performed at room temperature. The slurry concentration, i.e. the volume percent of sedimented particles in the solvent, may vary widely, usually between 1–100%. The coating procedure may be repeated one or more times when increased surface covering is needed.

In the above described first method embodiment, the particles in the slurry should be significantly less soluble in the solvent than the article surface to be coated, and are usually substantially insoluble in the solvent.

The second method embodiment may be performed by dipping the cleaned article in the solvent for a suitable period of time and then treating the article surface with the dry particles, for example, by powdering or spraying or by putting/pressing the article against a surface loosely covered with dry particles. The surface is then dried, for example, by ambient or heated air, heat radiation or in vacuo.

In the third method embodiment described above, the solvent with which the article surface is contacted prior to the contact with the particle slurry may or may not be the same as that of the slurry.

After the drying of the surfaces coated in accordance with either of the three method embodiments described, non-entrapped particles may be washed off from the surfaces, for example, by flushing first with ethanol and then with water.

The cleaning of the article surfaces prior to the coating procedures, may, for example, be performed by rinsing with water and then ethanol followed by drying, such as with or without warm air, in an oven or in vacuo.

The polymer based material of the article surface to be coated in accordance with the invention may be selected from a wide range of materials for which a suitable solvent exists. Suitable polymer/solvent combinations are readily apparent to the skilled person. Exemplary of polymers are polystyrene, polyvinylchloride, polymethyl methacrylate, polycarbonate, polyethylene terephthalate copolyester, and the like. Examples of suitable corresponding solvents are esters, aliphatic and aromatic hydrocarbons, halogenated hydrocarbons, ketones, and aliphatic and aromatic amines, such as e.g. triethylamine.

It is readily appreciated that the method of the present invention may be used to conveniently and efficiently provide an article surface with a considerably increased surface area as well as any desired property provided by the specific particles chosen. With respect to the attainable surface expansion the particles are preferably porous. Depending on the porosity and size of the specific particles, a surface enlargement of the order of 1000 times may readily be achieved.

The present technique of surface modification is applicable to a wide range of molecules, particles and supports and for a wide range of purposes. Surfaces modified in accordance with the invention may, for example, be used as surfaces for solid-phase reactions, biologically active surfaces, surfaces preactivated for subsequent coupling reactions, electrophoretic plate surfaces, diagnostic stick surfaces, surfaces for further functionalization or derivatization, etc.

An apparent advantage of coating a surface with particles in accordance with the invention is that molecules may be coupled to the particles batch-wise and the particles stored before the simple immobilization onto the article surface. It is, of course, also possible to derivatize the particles after they have been immobilized to the article surface, or both before and after immobilization, if desired.

The specific particles to be coated on the article surface will depend on the desired surface area enlargement and the specific property or properties to be provided to the article surface. The particles may, for example, be powdery polymers having properties like hydrophilicity, hydrophobicity, etc. Other examples are particles for chromatography (packings). The latter may for instance be hydrophilic, hydrophobic, anionic exchangers, cationic exchangers, biologically active (e.g. with coupled enzyme, DNA, antibody, antigen, etc), preactivated (for later coupling reactions). Exemplary of chromatographic particles are silica, polystyrene-divinylbenzene, acrylates and carbohydrate-based materials, such as e.g. cross-linked agarose and dextran. The method of the invention also provides for immobilizing different reagents on separate particles, bound to the same support.

Since the method of the invention does not involve any introduction of additional material, like e.g. an adhesive, to the article surface, the properties of the activated particles will be easier to maintain than in the prior art methods.

When the particles are porous, capillary action will insure that a small volume can be distributed over a large particle-coated surface without fully immersing the particle-carrying support. In this manner minimal reaction volumes can be used, reducing the requirement for reagents and minimizing diffusion distances. Experiments may thus be performed on the surface of the support without the requirement for any reservoir.

The invention will now be illustrated further by the following non-limiting Examples.

EXAMPLE 1

Polystyrene films, 35×12×0.2 mm, were washed by dipping first in 50% ethanol in water for 5 seconds and then in ethanol for 5 seconds followed by drying in a ventilated fume hood. The films were coated with silica particles (Sephasil™ C 8 Prep Grade, Pharmacia LKB Biotechnology AB, Uppsala, Sweden; spherical, porous, $C_8$ derivatized silica, $dp_{50}$(volume weighted (mass) median diameter)=12 μm) by dipping the films for 2 seconds in a stirred slurry of 5 g of silica particles in 10 ml acetone, 50% slurry. After 3 minutes drying in air, the films were redipped in the slurry for 2 seconds and allowed to dry in air for 5 minutes. Non-entrapped particles were washed off from the films by flushing with a wash bottle, first with ethanol and then with water. Specific surface area measuring (BET-equation, krypton) showed that the coated films had increased the area 800 times compared to uncoated films.

EXAMPLE 2

Films of polyethylene terephthalate copolyester, 35×12×0.4 mm, were cleaned as in Example 1. The films were coated with agarose beads (Superose® 12, Pharmacia LKB Biotechnology AB, Uppsala Sweden; spherical, porous, hydrophilic, cross-linked agarose beads, $dp_{50}$=10 μm) by dipping the films for 2 seconds in a stirred slurry of 1 g of Superose® 12 in 10 ml toluene, 50% slurry, followed by drying and washing as in Example 1.

EXAMPLE 3

Polymethyl methacrylate plates, 35×12×0.5 mm, were cleaned as in Example 1. The plates were coated with dextran beads (Sephadex® G-100 Superfine, Pharmacia LKB Biotechnology AB, Uppsala Sweden; spherical, porous, hydrophilic, cross-linked dextran beads, $dp_{50}$=10–40 μm) by dipping the plate for 5 seconds in chloroform and immediately pressing the plates on a surface covered with dry Sephadex®. After drying for 5 minutes, the plates were washed as in Example 1.

EXAMPLE 4

Polystyrene films, 35×12×0.2 mm, were cleaned as in Example 1. The films were coated with Superose® 12 (see Example 2) in acetone by:

A: dipping a film once in 20% slurry for 2 seconds, followed by 3 minutes air drying and then washing the film as in Example 1;

B: dipping a film once in 20% slurry for 2 seconds, followed by 3 minutes air drying, repeating the procedure twice and then washing the film as in Example 1;

C: dipping a film once in 50% slurry for 2 seconds, followed by 3 minutes air drying and then washing the film as in Example 1;

D: dipping a film once in 50% slurry for 2 seconds, followed by 3 minutes air drying, repeating the procedure once and then washing the film as in Example 1;

E: dipping a film once in 70% slurry for 2 seconds, followed by 3 minutes air drying and then washing the film as in Example 1.

Microscopic examination of the films showed the following order of covering: D>E,C>B>A.

EXAMPLE 5

A. Preparation of streptavidin-coupled agarose beads (SA-beads)

Steptavidin (Immunopure Streptavidin, Pierce, Rockford, Ill., U.S.A.; streptavidin is a protein, approximately 60,000 in molecular weight, consisting of four subunits, each containing a biotin binding site) was coupled to agarose beads (HiTrap® NHS-activated, Pharmacia LKB Biotechnology AB, Uppsala, Sweden; spherical, porous, hydrophilic, crosslinked agarose beads, Sepharose® High Performance, $dp_{50}$= 34 µm, preactivated with N-hydroxy-succinimide for coupling of proteins). 2 mg of streptavidin were coupled, according to the manufacturer's instruction manual for HiTrap® NHS-activated, to one ml of agarose beads, which corresponds to 33 pmol streptavidin/µl beads.

B. Coating of films with SA-beads

Polystyrene films, 9×4×0.2 mm, were cleaned as in Example 1. Part of each film was coated with SA-beads prepared in section A above by dipping the film, to a depth of 3 mm, for 2 seconds in a stirred slurry of SA-beads in acetone, 75% slurry. After 10 minutes drying in air, non-entrapped beads were washed off by flushing with water, then the films were allowed to dry in air.

C. Test of biotin binding capacity

The biotin binding capacity of (i) the SA beads prepared in section A above and (ii) the SA-bead coated films prepared in section B above was measured with $^3$H-labelled biotin (TRK 753, Amersham, England). The SA-beads had a capacity of 115 pmol biotin/µl SA-beads. The coated films showed a capacity of 48 pmol biotin/film (coated area: 26 mm$^2$, which corresponds to approximately 1 µl of SA-beads with part of their surface faced to the film). Films coated with agarose beads without streptavidin showed no binding of biotin.

This demonstrates that the biochemical activity of the SA-coated beads was maintained after the films had been coated therewith in accordance with the invention.

The invention is, of course, not restricted to the above specifically described embodiments, but many changes and modifications can be made within the scope of the general inventive concept as defined in the following claims.

What is claimed is:

1. A method of modifying a synthetic polymer based surface having a top surface and made from the synthetic polymer by coating the surface with polymer particles, which method comprises (a) converting the top surface layer of the polymer based surface to a swollen or semidissolved state with a solvent and without the use of an adhesive for the particles;

(b) simultaneously or subsequently to step(a) contacting the swollen or semidissolved polymer based surface with the polymer particles to partially embed the particles in the polymer based surface, wherein the polymer particles are either dry or in a slurry; and (c) drying the surface subsequent to contact with the polymer particles;

wherein the polymer particles are derivatized either prior to or subsequent to step (b).

2. The method according to claim 1, wherein said solvent and said polymer particles are simultaneously contacted with said synthetic polymer based surface.

3. The method according to claim 1, wherein step(b) is carried out subsequently to step (a).

4. The method according to claim 1, wherein said particles are porous.

5. The method according to claim 1, wherein said particles are particles for chromatography.

6. The method according to claim 1, wherein said particles are selected from the group consisting of hydrophilic materials, hydrophobic materials, anion-exchange materials, cation-exchange materials, biologically active materials, and materials which are activated so as to be capable of coupling.

7. The method according to claim 1, wherein said synthetic polymer based surface comprises a polymer selected from the group consisting of polystyrene, polycarbonate, polyvinylchloride, polymethyl methacrylate and polyethylene terephthalate copolyester.

8. The method according to claim 2, wherein said solvent is selected from the group consisting of esters, aliphatic and aromatic hydrocarbons, halogenated hydrocarbons, aliphatic amines, aromatic amines, and ketones.

9. The method of claim 1, wherein said particles are present in a monolayer on said surface.

10. The method of claim 1, wherein said polymer particles have a $dp_{50}$ in the range of 10–40 µm.

* * * * *